US00PP27175P2

(12) United States Plant Patent
Eveleens

(10) Patent No.: US PP27,175 P2
(45) Date of Patent: Sep. 20, 2016

(54) CARNATION PLANT NAMED 'HILPROT'

(50) Latin Name: *Dianthus caryophyllus*
Varietal Denomination: Hilprot

(71) Applicant: Peter Eveleens, Aalsmeer (NL)

(72) Inventor: Peter Eveleens, Aalsmeer (NL)

(73) Assignee: HILVERDA KOOIJ B.V., De Kwakel (NL)

( * ) Notice: Subject to any disclaimer, the term of this patent is extended or adjusted under 35 U.S.C. 154(b) by 93 days.

(21) Appl. No.: 14/120,583

(22) Filed: Jun. 6, 2014

(51) Int. Cl.
*A01H 5/02* (2006.01)

(52) U.S. Cl.
USPC ..... Plt./272

(58) Field of Classification Search
USPC ..... Plt./272, 273
See application file for complete search history.

*Primary Examiner* — June Hwu
(74) *Attorney, Agent, or Firm* — C. A. Whealy

(57) ABSTRACT

A new and distinct cultivar of Carnation plant named 'Hilprot', characterized by its upright, outwardly spreading and uniformly mounded plant habit; freely branching habit; freely flowering habit; large purple-colored double flowers with light pink-colored margins that are positioned above and beyond the foliar plane on strong peduncles; and good garden performance.

1 Drawing Sheet

Botanical designation: *Dianthus caryophyllus.*
Cultivar denomination: 'HILPROT'.

BACKGROUND OF THE INVENTION

The present invention relates to a new and distinct cultivar of Carnation plant, botanically known as *Dianthus caryophyllus*, grown commercially as a potted and garden plant and hereinafter referred to by the name 'Hilprot'.

The new Carnation plant is a product of a planned breeding program conducted by the Inventor in De Kwakel, The Netherlands. The objective of the breeding program is to create new potted Carnation plants that have uniform plant habit and numerous attractive flowers.

The new Carnation plant originated from a cross-pollination made by the Inventor in De Kwakel, The Netherlands in June, 2009 of a proprietary selection of *Dianthus caryophyllus* identified as code number 2318160782, not patented, as the female, or seed, parent with *Dianthus caryophyllus* 'Margarita', disclosed in U.S. Plant Pat. No. 17,335, as the male, or pollen, parent. The new Carnation plant was discovered and selected by the Inventor as a single flowering plant from within the progeny of the stated cross-pollination in a controlled greenhouse environment in De Kwakel, The Netherlands in September, 2010.

Asexual reproduction of the new Carnation plant by terminal cuttings propagated in a controlled greenhouse environment in De Kwakel, The Netherlands since October, 2010 has shown that the unique features of this new Carnation plant are stable and reproduced true to type in successive generations of asexual reproduction.

SUMMARY OF THE INVENTION

Plants of the new Carnation have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Hilprot'. These characteristics in combination distinguish 'Hilprot' as a new and distinct Carnation plant:

1. Upright, outwardly spreading and uniformly mounded plant habit.
2. Freely branching habit.
3. Freely flowering habit.
4. Large purple-colored double flowers with light pink-colored margins that are positioned above and beyond the foliar plane on strong peduncles.
5. Good garden performance.

Plants of the new Carnation differ from plants of the female parent selection in the following characteristics:

1. Plants of the new Carnation are more outwardly spreading than and not as upright as plants of the female parent selection.
2. Plants of the new Carnation have longer lateral branches then plants of the female parent selection.
3. Plants of the new Carnation flower a few days earlier than plants of the female parent selection.
4. Flower petals of plants of the new Carnation are more rounded than flower petals of plants of the female parent selection.

Plants of the new Carnation differ from plants of the male parent, 'Margarita', in the following characteristics:

1. Plants of the new Carnation have broader leaves than plants of 'Margarita'.
2. Flowers of plants of the new Carnation have more petals per flower than flowers of plants of 'Margarita'.
3. Flower petals of plants of the new Carnation are more rounded than flowers petals of plants of 'Margarita'.
4. Plants of the new Carnation and 'Margarita' differ slightly in flower color.

Plants of the new Carnation can be compared to plants of *Dianthus caryophyllus* 'Hilbreye', disclosed in U.S. Plant Pat. No. 24,340. In side-by-side comparisons conducted in De Kwakel, The Netherlands, plants of the new Carnation differed from plants of 'Hilbreye' in the following characteristics:

1. Plants of the new Carnation were more outwardly spreading than and not as upright as plants of 'Hilbreye'.
2. Plants of the new Carnation had smaller flowers than plants of 'Hilbreye'.
3. Plants of the new Carnation and 'Hilbreye' differed slightly in flower color.

BRIEF DESCRIPTION OF THE PHOTOGRAPH

The accompanying photograph illustrates the overall appearance of the new Carnation plant showing the colors as true as it is reasonably possible to obtain in colored reproductions of this type. Colors in the photograph may differ slightly from the color values cited in the detailed botanical description which accurately describe the colors of the new Carnation plant.

The photograph comprises a side perspective view of a typical flowering plant of 'Hilprot' grown in a container.

DETAILED BOTANICAL DESCRIPTION

Plants used in the aforementioned photograph and following observations and measurements were grown during the late winter and early spring in 12-cm containers in a glass-covered greenhouse in De Kwakel, The Netherlands and under cultural practices typical of commercial potted Carnation production. During the production of the plants, day and night temperatures averaged 12° C. and light levels averaged 7 klux. Plants were pinched one time five weeks after planting. Plants used for the description were 20 weeks old and plants used for the photograph were 25 weeks old. In the following description, color references are made to The Royal Horticultural Society Colour Chart, 2007 Edition, except where general terms of ordinary dictionary significance are used.

Botanical classification: *Dianthus caryophyllus* 'Hilprot'.

Parentage:

*Female, or seed, parent*.—Proprietary selection of *Dianthus caryophyllus* identified as code number 2318160782, not patented.

*Male, or pollen, parent*.—*Dianthus caryophyllus* 'Margarita', disclosed in U.S. Plant Pat. No. 17,335.

Propagation:

*Type*.—By terminal cuttings.

*Time to initiate roots, summer*.—About six days at temperatures about 20° C. to 25° C.

*Time to initiate roots, winter*.—About eight days at temperatures about 18° C.

*Time to produce a rooted young plant, summer*.—About three weeks at temperatures about 20° C. to 25° C.

*Time to produce a rooted young plant, winter*.—About five weeks at temperatures about 18° C.

*Root description*.—Medium in thickness, fibrous; white in color.

*Rooting habit*.—Moderate branching; medium density.

Plant description:

*Plant type and form*.—Herbaceous perennial; upright, outwardly spreading and uniformly mounded plant habit; flattened globular.

*Branching habit*.—Freely-branching growth habit; when pinched, about seven primary branches develop, each with about five secondary branches; dense and bushy growth habit.

*Plant height*.—About 15.9 cm.

*Plant diameter or spread*.—About 33.3 cm.

*Lateral branches*.—Length: About 13.3 cm. Diameter: About 3 mm. Internode length: About 2.2 cm. Strength: Strong. Texture: Smooth, glabrous; waxy. Color: Close to N137A; waxy cuticle, close to 188A and 189A. Stem shape: Circular. Stem interior: Solid.

Leaf description:

*Arrangement*.—Opposite, simple; sessile.

*Length*.—About 10.8 cm.

*Width*.—About 8 mm.

*Shape*.—Narrowly oblanceolate to lanceolate, curved.

*Apex*.—Acute.

*Base*.—Attenuate, decurrent.

*Margin*.—Entire.

*Texture, upper and lower surfaces*.—Smooth, glabrous; waxy.

*Venation pattern*.—Parallel.

*Color*.—Developing leaves, upper and lower surfaces: Close to 143C; towards the base, close to 144B. Fully expanded leaves, upper surface: Close to N137C; waxy cuticle, close to 189B; venation, close to 143B. Fully expanded leaves, lower surface: Close to N137C; waxy cuticle, close to 189B; venation, close to to 144A.

Flower description:

*Flower type and habit*.—Rotate double flowers, flowers typically solitary or occasionally in pairs or clusters of four; freely flowering habit with typically about 42 flowers developing per plant; flowers positioned above and beyond the foliar plane on strong peduncles; flowers face mostly upright to outwardly.

*Fragrance*.—Faintly fragrant; clove-like, sweet.

*Natural flowering season*.—Flowering is continuous through the summer and late summer in The Netherlands; plants begin flowering about twelve weeks after planting.

*Flower longevity*.—Flowers last about ten days on the plant; flowers not persistent.

*Flower diameter*.—About 4.7 cm.

*Flower depth*.—About 4.3 cm.

*Flower buds*.—Length: About 2.5 cm. Diameter: About 1 cm. Shape: Elliptic to oblong; styles not extruded. Color: Close to 137A; base, close to 143B and 144A.

*Petals and petaloids*.—Quantity and arrangement: About 20 petals and petaloids per flower arranged in numerous whorls. Length: About 4.3 cm. Width: About 2.2 cm. Shape: Spatulate. Apex: Praemorse, crinkled; incisions, medium to many in quantity and shallow in depth. Base: Acute. Margin: Entire. Texture, upper and lower surfaces: Smooth, glabrous; velvety. Color: When opening, upper surface: Close to between 187A and 203A; margins, close to 75C to 75D and N57A; at the base, close to 145D. When opening, lower surface: Close to N77B; margins, close to 75B to 75C; at the base, close to 145D. Fully opened, upper surface: Slightly darker than 187A; margins, close to 69B to 69C; towards the base, close to 60B and 61B; at the base, close to 145D; color does not fade with development. Fully opened, lower surface: Close to N77B; margins, close to 62C to 62D; at the base, close to 145D.

*Sepals*.—Quantity and arrangement: Five in a single whorl; proximal 60% of the sepals are fused into a campanulate-shaped calyx; epicalyx, adpressed to calyx, individual segments are deltoid in shape with short acute apices. Length: About 2.4 cm. Width: About 6 mm. Shape: Oblong. Apex: Broadly acute. Margin: Entire. Texture, upper and lower surfaces: Smooth, glabrous. Color: When opening, upper surface: Close to 138C. When opening, lower surface: Close to 137A; towards the base, close to 143B and 144A. Fully opened, upper surface: Close to 138C. Fully opened, lower surface: Close to N137C; towards the base, close to 143B and 144A.

*Peduncles*.—Length: About 1.7 cm. Diameter: About 3 mm. Strength: Strong. Aspect: Mostly erect. Texture: Smooth, glabrous; waxy. Color: Close to N137A; waxy cuticle, close to 188A and 189A.

*Reproductive organs*.—Stamens: Quantity: About three, mostly deformed. Filament length: About 1.5 cm. Filament color: Close to 157D. Anther length: About 2 mm. Anther shape: Irregularly oblong. Anther color: Close to 155A. Pollen: None observed. Pistils: Quantity: About two per flower. Pistil length: About 3.1 cm. Stigma shape: Pointed, curved. Stigma color: Close to 70C. Style length: About 2.8 cm. Style color: Close to 155A. Style shoulder: None. Ovary color: Close to 145C. Ovary shape: Ovoid. Ovary texture: Slightly ribbed. Fruits and seeds: Fruit and seed development have not been observed on plants of the new Carnation.

Disease & pest resistance: Plants of the new Carnation have not been observed to be resistant to pathogens and pests common to Carnation plants.

Garden performance: Plants of the new Carnation have been observed to have good garden performance and to tolerate wind, rain and temperatures ranging from about 5° C. to about 35° C. and to be hardy to USDA Hardiness Zone 9.

It is claimed:

1. A new and distinct Carnation plant named 'Hilprot' as illustrated and described.

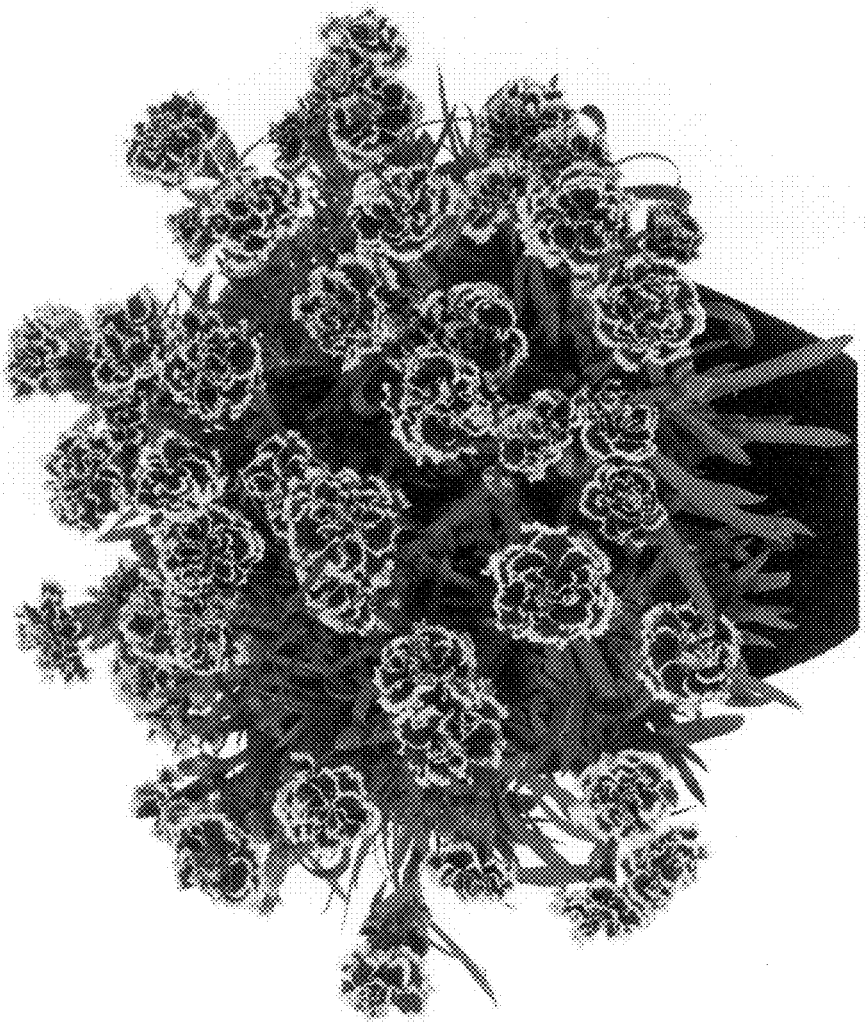

* * * * *